United States Patent [19]

Columbus

[11] 4,413,407

[45] Nov. 8, 1983

[54] METHOD FOR FORMING AN ELECTRODE-CONTAINING DEVICE WITH CAPILLARY TRANSPORT BETWEEN ELECTRODES

[75] Inventor: Richard L. Columbus, Rochester, N.Y.

[73] Assignee: Eastman Kodak Company, Rochester, N.Y.

[21] Appl. No.: 319,568

[22] Filed: Nov. 9, 1981

Related U.S. Application Data

[60] Division of Ser. No. 128,413, Mar. 10, 1980, Pat. No. 4,302,313, and a continuation-in-part of Ser. No. 59,816, Jul. 23, 1979, abandoned, which is a continuation-in-part of Ser. No. 954,689, Oct. 25, 1978, Pat. No. 4,233,029.

[51] Int. Cl.³ ............................................. H01R 43/00
[52] U.S. Cl. .................................. 29/825; 156/244.25; 156/292; 324/438
[58] Field of Search ............. 29/825, 592; 204/195 R, 204/195 B, 195 L, 195 G, 195 M; 324/425, 438, 439, 450; 156/244.22, 244.25, 292

[56] References Cited

U.S. PATENT DOCUMENTS

| | | | |
|---|---|---|---|
| 3,528,903 | 9/1970 | Taylor | 204/435 |
| 3,690,836 | 9/1972 | Buissiere et al. | 23/253 |
| 3,715,192 | 2/1973 | Wenz et al. | 422/56 |
| 3,763,422 | 10/1973 | MacPhee et al. | 324/438 |
| 3,783,696 | 1/1974 | Coleman | 73/425.4 |
| 3,826,734 | 7/1974 | Godsey, Jr. | 204/299 R |
| 3,891,507 | 6/1975 | Breuer | 195/103.5 |
| 4,046,514 | 9/1977 | Johnston et al. | 422/56 |
| 4,053,381 | 10/1977 | Hamblen et al. | 204/195 |
| 4,184,936 | 1/1980 | Paul et al. | 204/195 R |
| 4,273,639 | 6/1981 | Gottermeier | 204/195 |
| 4,310,399 | 1/1982 | Columbus | 204/195 |

FOREIGN PATENT DOCUMENTS

| | | | |
|---|---|---|---|
| 865849 | 3/1971 | Canada | 324/438 |
| 1008507 | 4/1977 | Canada . | |
| 2555958 | 12/1975 | Fed. Rep. of Germany | 204/1 R |
| 2396299 | 6/1978 | France . | |

OTHER PUBLICATIONS

Research Disclosure, vol. 175, Pub. No. 17517, Nov. 1978.

Primary Examiner—Francis S. Husar
Assistant Examiner—Carl J. Arbes
Attorney, Agent, or Firm—Dana M. Schmidt

[57] ABSTRACT

A device suitable for potentiometric analysis of liquid ions is disclosed, wherein a liquid transport member extending between and adjacent to two electrodes comprises two opposed surfaces spaced apart a distance to induce capillary flow of liquid between the surfaces.

5 Claims, 28 Drawing Figures

METHOD FOR FORMING AN ELECTRODE-CONTAINING DEVICE WITH CAPILLARY TRANSPORT BETWEEN ELECTRODES

RELATED APPLICATIONS

This is a division of application Ser. No. 128,413, filed Mar. 10, 1980, now U.S. Pat. No. 4,302,313, issued Nov. 24, 1981 and a continuation-in-part of application Ser. No. 059,816, filed July 23, 1979, now abandoned which is a continuation-in-part of application Ser. No. 954,689, filed Oct. 25, 1978, now U.S. Pat. No. 4,233,029, issued Nov. 11, 1980.

FIELD OF THE INVENTION

This invention relates to a device for determining the activity and therefore the concentration of electrolytes in a liquid. Such devices are valuable quantitative tools in the field of clinical chemistry to determine the existence and cause of certain body illnesses and abnormalities.

BACKGROUND OF THE INVENTION

Recently a disposable test device was developed fo the potentiometric analysis of blood serum using two identical ion-selective electrodes (hereinafter, "ISE's"). Examples of such devices are disclosed in U.S. Pat. No. 4,053,381, issued Oct. 11, 1977. The ISE's of such a device are overlaid or otherwise contacted with an ion bridge that provides for ionic flow between a drop of a test liquid and a drop of a reference liquid, the bridge also having apertures allowing the drops to contact their respective electrodes. When an electrometer or potentiometer makes contact with both electrodes, a differential potential is detected that is proportional to the difference in activity, and therefore concentration, of the ion under analysis. An embodiment useful for absolute measurements is also disclosed.

Such a device has permitted rapid, automatic measurements of electrolytes using very small samples of serum. Although such advantages have constituted marked improvements, there have remained certain aspects that are subject to further improvement. In one form of the device, the bridge between the electrodes has comprised an absorbent matrix open to the atmosphere, causing evaporation and loss of, or contamination by, analytes such as $CO_2$. In another form, the ion bridge has comprised a fibrous matrix the fibers of which are not always restricted to desired orientations. Occassionally such fibers can extend out from the bridge and contact one or more underlayers of the electrode. When a portion of the liquid to be tested wets such fibers, the ISE can become shorted.

Yet another drawback with certain materials used as an ion bridge has been their inability to transport whole blood. For example, a fibrous matrix such as most paper materials has capillary passageways which are too tortuous for the transport of whole blood without hemolysis. The alternative of course is to phase-separate the serum, a time-consuming additional step.

Therefore, prior to this invention there has been an unsatisfied need for an ion bridge that does not utilize fibrous materials as the primary transport media but does allow for the transport of whole blood.

OTHER RELATED APPLICATIONS

My U.S. application Ser. No. 101,662, entitled "Liquid Transport Device Containing Means for Delaying Capillary Flow", filed on Dec. 10, 1979, now U.S. Pat. No. 4,310,399, issued on Jan. 12, 1982, discloses a liquid transport device in general wherein two opposing surfaces are provided with gating means extending across the zone to delay flow of liquid therewithin.

Commonly-owned U.S. application Ser. No. 050,845, filed on June 20, 1979, by W. Gottermeier entitled "Capillary Bridge in Apparatus for Determining Ionic Activity," now U.S. Pat. No. 4,273,639, issued on June 16, 1981, discloses a device for potentiometric measurements wherein the bridge is a porous material encapsulated in a member that is also the frame that mounts a pair of ISE's.

SUMMARY OF THE INVENTION

This invention is directed to a device which provides for improved controlled flow of liquid, such as serum or serum equivalents, in a manner that solves the aforementioned problems in the transport of liquid to electrodes.

More specifically, in one aspect of the invention there is provided an improved device for determining the activity of an ionic analyte of a liquid, the device including a pair of solid electrodes each constructed to generate an electrical potential that is proportional to analyte activity of a contacting quantity of such a liquid, and flow control means for directing flow of a quantity of such liquid to at least one of the electrodes. The device is improved by including in the control means, (a) two opposed liquid transport surfaces extending from a first location disposed adjacent one of the electrodes to a second location adjacent the other of the electrodes, the surfaces being spaced apart a distance effective to induce capillary flow between the surfaces of introduced liquid and thus to create a transport zone, the transport zone being in liquid communication with the electrodes and having a void volume that is at least about 50% of the volume of said zone; and (b) means defining a liquid passageway extending from an exterior surface of the device to the zone; whereby a quantity of a liquid deposited in the passageway flows into contact with an electrode.

In another aspect of the invention, there is provided a multi-analyte test device for the analysis of a plurality of different ionic analytes in a quantity of a liquid, the device comprising, a first sheet, a second covering sheet, the sheets having opposing surfaces, means for spacing apart the sheets a distance effective to induce capillary flow between the surfaces of introduced liquid and to create a transpot zone, one of the sheets including means permitting introduction of a quantity of liquid into the zone, and a plurality of electrically isolated electrodes disposed in liquid communication with the zone, at least a first one of the electrodes comprising a test composition specific to the analysis of one of the analytes, and at least a second of the electrodes comprising a test composition specific to the analysis of a different one of the analytes, and vent means for permitting air to exit from the zone ahead of advancing liquid.

Characterized in another manner, the invention provides a method for making such a device, comprising the steps of (a) providing a first sheet of formable material having a width and length;

(b) forming in the sheet a plurality of adjacent channels extending generally the length of the sheet, a surface of one of the channels being configured to transport liquid, (c) superimposing above the formed sheet a second sheet a surface portion of which is configured to transport liquid and is opposite to and spaced away from the one channel surface a distance effective to induce capillary flow of the liquid between the portion and the one surface;

(d) securing the second sheet to the first sheet to define a capillary liquid transport zone extending in the direction of the length of the first sheet;

(e) forming apertures extending all the way through the secured first and second sheets;

(f) severing individual units from the apertured, secured sheets; and (g) attaching a pair of said electrodes to each of the severed units at an exterior surface of the first sheet.

Thus, one advantage of the present invention is that an ion-selective electrode device can be provided with a bridge between the electrodes capable of providing controlled flow of liquid while avoiding the use of materials that tend to cause shorts across the electrode.

In a related advantage of the invention, there is provided such a device which allows whole blood to be tested for ionic analytes.

In still another aspect of the invention, such a device is provided which prevents excessive air contact with the liquid during testing, such as could cause evaporation and/or contamination.

Yet another aspect of the invention is a method of manufacturing such devices in a manner conducive to a continuous process.

Other features and advantages will become apparent upon reference to the following Description of the Preferred Embodiments when read in light of the attached drawings.

DESCRIPTION OF THE PREFERRED EMBODIMENTS

The device of this invention is capable of measuring the activity of various ionic analytes, commonly called electrolytes, found in liquids such as aqueous solutions. From this measurement the corresponding concentration of the analyte is calculated by known methods using calibrated relationships.

The embodiments hereinafter described refer to whole blood or blood serum as the preferred test solution. In addition, any aqueous solution can be measured, including other biological liquids and industrial liquids. Examples of biological liquids include blood plasma, urine and spinal fluid.

Preferably, liquid is deposited on the device of the invention in the form of drops, as discussed below. In addition, any other form of the liquid can be used to introduce the necessary quantity for flow and for testing.

It has been discovered that an improved liquid transport device can be provided to direct the flow of a test drop to an electrode for potentiometric measurement. Such measurement can be done either differentially or "absolutely", the differential mode being the preferred mode. As is explained in the aforesaid U.S. Pat. No. 4,053,381, these two modes differ primarily depending on whether a drop of a known reference liquid is deposited along with the test sample drop, or not, respectively. In accordance with the invention, a device 10 for differentially measuring electrolytes comprises, FIGS. 1-3, an electrically insulative frame 12 which mounts a spaced-apart pair of preferably solid ion-selective electrodes 14, 14' (hereinafter, "ISE's") spanned by a flow control bridge 36. As described in detail in U.S. Pat. No. 4,053,381, issued on Oct. 11, 1977, the details of which are expressly incorporated herein by reference, each ISE is a generally flat multilayered element comprising adjacent layers 16–20, FIG. 2. When a drop of blood serum A or B, FIG. 2, makes contact with layer 16, an ion-selective membrane containing an ionophore and a solvent, the $Z \oplus$ of choice is carried or otherwise effectively penetrates to the underlying layers 17–18 where an electrical potential is generated proportional to the activity of that particular ion. Layer 17, for example, can be a dried hydrophilic binder containing the salt $Z \oplus X \ominus$. Layer 18 in such instances is the $X \ominus$ salt of an electrically conductive metal $M \oplus$, and metal $M°$ forms layer 19. Because layer 19 is an electrically conductive layer, a potential can be detected by electrometer 26, FIG. 1, via probes 24 which penetrate into contact with layer 19 at windows 22. Any difference in these potentials due to two different ion activities of two liquids A and B, one an unknown and one a reference having a known concentration of $Z \oplus$, is registered as a difference potential on the electrometer. This reading then is converted into a measure of concentration of the ionic analyte $Z \oplus$.

Figure 2:
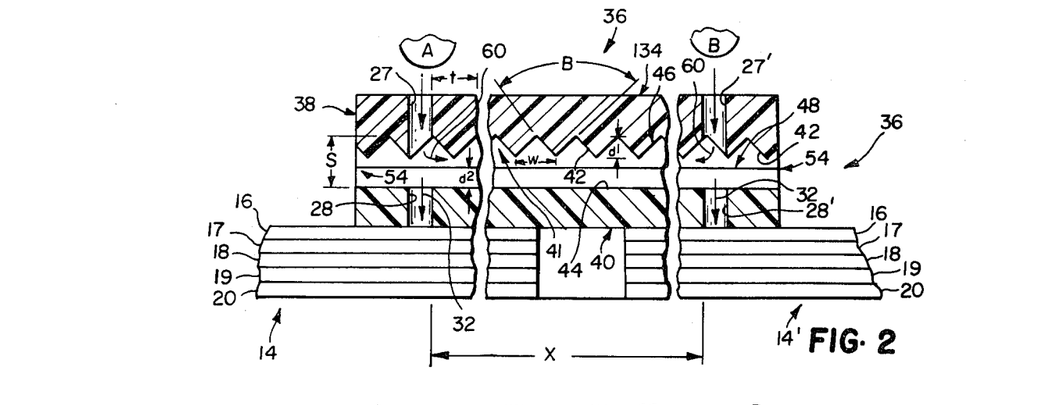
FIG. 2 is a sectional view taken generally along the vertical plane through line II—II of FIG. 1.

In this embodiment of the invention the flow control means comprises bridge 36 that provides means for directing the liquid flow from drops A and B to ISE's 14 and to each other, FIG. 2. By such means, an electrical circuit is completed and the difference in the potentials generated in the ISE's will register on electrometer 26. The bridge in turn comprises two members 38 and 40 spaced apart in the manner described below to form a transport zone 41. To introduce drops A and B into zone 41, passageways formed as apertures 27 and 27' are located in member 38. To provide liquid communication between zone 41 and ISE's 14 and 14', apertures 28 and 28' are positioned above and adjacent to the respective ISE 14 and 14' to be contacted by the liquid.

Any convenient drop dispenser can supply the drops, either in free-falling form or as drops touched-off from a platform. Preferably, the drops are dispensed approximately at the same time to insure proper junction formation, as described below.

In accordance with one aspect of the invention, members 38 and 40 have opposing internal surfaces spaced apart a distance "s" effective to induce capillary flow of liquid between the surfaces and to define the transport zone 41. Apertures 27 and 27' are sized to insure that the drops penetrate into the apertures and wet both of these opposing surfaces. In one embodiment of the invention, each surface bears a pattern of exposed grooves 42 and 44, which can be, for example, sawtooth in shape. Grooves 44 extend from at least the vicinity of aperture 28 to at least the vicinity of aperture 28', and are preferably substantially parallel and straight. Grooves 42 are superimposed over grooves 44 preferably at a positive, that is, non-zero angle "alpha", FIG. 3. Most preferably alpha is about 90°, and the grooves are also substantially parallel and straight along their lengths. As shown, grooves 42 and their ridges 46 have a width "w" and thickness "t", respectively, of about 13 microns. The same or different dimensions can be used for grooves 44 and their ridges. Grooves 42, FIG. 2, represent a groove pattern as it would appear magnified approximately 700 times.

Figure 1:
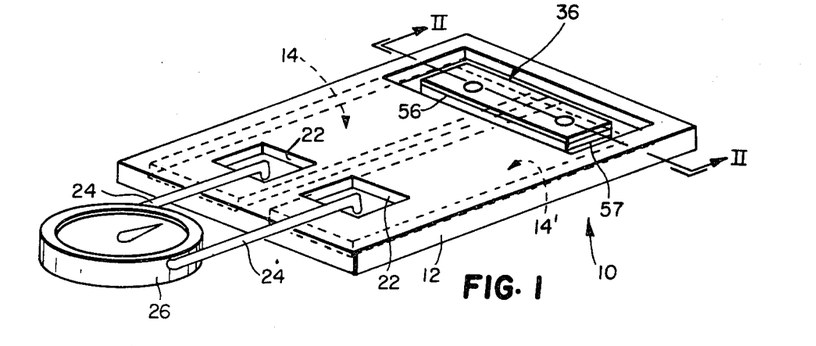
FIG. 1 is an isometric view of an ISE test device constructed in accordance with the invention.

Member 38 is spaced from member 40 by any suitable means, such as edge walls 54, so that grooves 42 are spaced from grooves 44 the effective distance that provides capillary flow. Walls 54 can be affixed to member 40 by means such as adhesive. Preferably, at least a portion of the space between grooves 42 and 44 is left exposed at one or both of zone edges 56 and 57 of bridge 36, FIG. 1, whereby air can be vented or expelled as liquid menisci advance.

Where exposed, the edges 56 and 57, FIG. 1, represent an energy barrier to further flow of the liquid. That is, the line of intersection between the edges 56 and 57 and the opposed surfaces represents a discontinuity beyond which capillary flow of the liquid can not proceed. Thus, leakage of the bridge is avoided.

Alternatively, the two members can be welded together at appropriate positions, such as by ultrasonic welding to form bridging studs that space the members apart. For example, such welding of the two members at pairs of relatively small spots 58, shown on phantom FIG. 3, provides the desired spacing.

If flow of the advancing wave fronts needs to be further restricted, the welding spots can be widened and located between apertures 27 and 27b' to create a barrier for each wave front with a restricted gating aperture for retarded flow-through.

Figure 3:
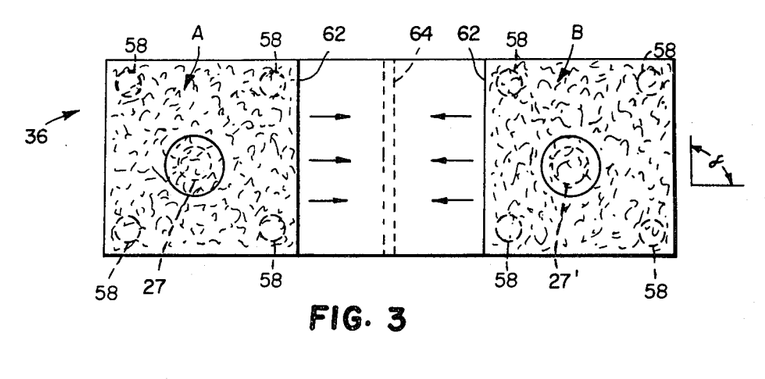
FIG. 3 is a plan view of the ion bridge of the device of FIGS. 1 and 2, illustrating the spreading pattern of liquid within the bridge.

Thus, the applied drops not only penetrate apertures 28 and 28', FIG. 2, as shown by arrows 32, to contact ISE's 14 and 14', they also flow along paths designated by arrows 60 to form two advancing wave fronts 62, FIG. 3, that flow in a predictable manner with a predetermined peripheral wave front configuration. Because grooves 42 and ridges 46 are linear, so are wave fronts 62. Because ridges 46, FIG. 2, are parallel throughout bridge 36, the wave fronts when they meet form a junction 64, FIG. 3, shown in phantom.

Grooves 42 and 44 and their ridges 46 and 48 have a number of dimensions which can be varied depending on the desired rate of flow of a particular liquid, as will be apparent to one skilled in the art. These dimensions are the grooves' width w, the ridges' thickness t and surface spacing s, already mentioned, the depths $d_1$ and $d_2$ of grooves 42 and 44, respectively, the included angle beta of ridges 46, and the angle of intersection alpha between the two sets of grooves (FIG. 3). In all cases, capillary flow should be maintained across the opposing surfaces of members 38 and 40 within transport zone 41, and preferably within the grooves 42 and 44, at a rate that is consistent with the intended end use. For uses that contemplate certain lesser flow rates, spacing s can be no greater than $d_1$ and $d_2$, that is, the top portions of ridges 46 can contact, not shown, the top portions of ridges 48. However, in such instances w should be selected so that multidirectional flow will be achieved notwithstanding a value for s equal to only $d_1$ plus $d_2$. If w is reduced below such larger values, when $s = d_1$ plus $d_2$, the transport time or time of spreading can become prolonged beyond useful values.

The width w of grooves 42, for example, does partially control, along with depth $d_1$ or $d_2$, the rate of advance of the liquid within those grooves. The rate has been found to vary roughly as an inverse function of the cross-sectional area of the groove that is tansverse to the flow along the length of that groove. That is, the smaller the transverse cross-sectional area of flow through a groove, the faster is the rate of advance of the liquid along that groove, because of capillary action. Furthermore, where the grooves 42 and 44 have uniform, cross-sectional areas different one from the other, the direction of the grooves (measured lengthwise) having the smaller value of that area will be the dominant flow direction.

Preferably, to insure a minimum of mixing of the two liquids at the junction 64, FIG. 3, the grooves 42 and 44 are respectively sized so that grooves 42 fill to their zonal edges 56 first, before junction 64 forms.

Included angle beta of ridges 46 or 48 is preferably between about 10° and about 100°, most preferably about 90°.

Angle alpha can be varied even to the point of equaling zero. In such a case, however, apertures 27 and 28 should have a spacing from apertures 27' and 28', such as distance "x", FIG. 2, sufficient to insure that each drop starts to spread from its aperture towards the other drop within the transport zone before the other drop reaches that aperture. Otherwise, for example, drop A from aperture 27 will flow into contact with ISE 14' causing contamination, and junction 64 will not form. It is to avoid this problem that the preferred value of alpha is selected to be about 90°. The exact value for the lateral spacing of the apertures depends on the value of alpha (i.e., how close it is to zero), the size of the grooves, and the surface tension of the liquid under analysis.

Furthermore, the cross-sectional shape of grooves 42 and 44 need not be saw-toothed as shown, but can be varied. For example, they can be rounded and ridges 46 can be truncated.

In the transport of blood serum, such as in the above-described use, it is preferred that the groove pattern variables of bridge 36 be chosen as follows. For grooves having a depth $d_1$ of between about 3 and about 15 microns, $w=t$, and a $w/d_1$ ratio between about 0.35 and about 7.5, the effective spacing s between the two surfaces can be varied between about 0.06 mm and about 0.6 mm for best results. Lesser values of s can be used, except that when the separation distance s approaches $d_1$ plus $d_2$, spreading through the zone becomes extremely delayed. Values of s greater than about 0.6 mm can in some cases destroy the capillary effect and thus the control over the wave front shape and rate of movement.

A preferred range for the width w of the grooves is between about 5 microns and about 5 mm, it being noted that beyond about 5 mm, the rate and direction of spreading becomes so ill-defined as to be insignificantly different from the results achieved by two smooth surfaces.

A representative example within the aforedescribed ranges of w, t, s, beta, $d_1$ and $d_2$ for the above-described potentiometric analysis of blood serum is as follows:

Example 1 w (for member 38) = 13.3 microns
w (for member 40) = 13.3 microns
t (for surface 12b) = 13.3 microns
t (for surface 14b) = 13.3 microns
s = 63.6 microns
beta = 90°
$d_1$ = 6.8 microns
$d_2$ = 6.8 microns
Distance x between apertures, FIG. 2 = 7 mm.

Preferred materials for at least the opposing surfaces of members 38 and 40, that is for the surfaces of grooves 42 and 44, are non-fibrous material that are substantially impervious to blood serum. Examples of such materials include acetates such as cellulose triacetate, cellulose acetate propionate, and cellulose acetate butyrate; polystyrene; polyethylene; polypropylene; ABS plastic; and polycarbonate. Such surface materials permit various chemical coatings to be applied, if desired, for example, surfactants.

It will be appreciated that a primary advantage of the construction of zone 41 as described above is its generally open configuration that nevertheless provides a controlled flow. Such a configuration leaves ample room for the flow of whole blood, unlike devices which utilize porous absorbent bridge means with void volumes less than about 50%. Furthermore, the materials described in the preceding paragraph, by being free of fibers, avoid the possibility of shorting out the ISE's.

Because the total environment is generally a closed one, evaporation from, and contamination of, zone 41 are minimized.

Figure 4:
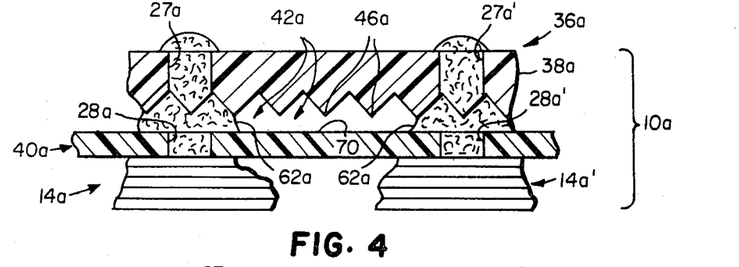
FIGS. 4 and 5a are fragmentary sectional views similar to that of FIG. 2 but illustrating alternate embodiments.
Figure 5A:
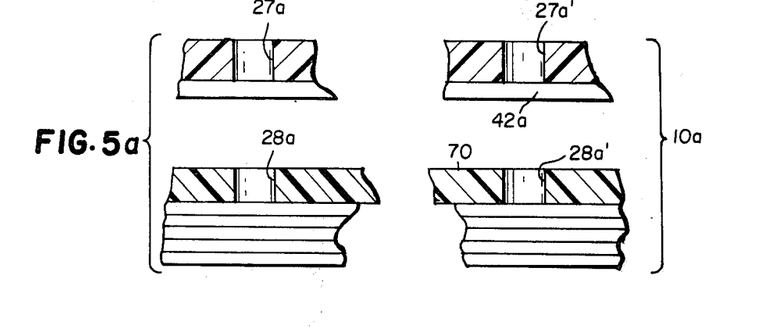

Alternatively, as in the embodiments shown in FIGS. 4 and 5a, at least one of the opposing surfaces forming the transport zone can be completely smooth. Parts similar to those previously described bear the same reference numeral to which the distinguishing suffix "a" is appended. Thus, device 10a and bridge 36a, FIG. 4, are generally identical to the device and bridge of the previous embodiment, for example, apertures 27a, 27a', 28a and 28a' provide flow of the two drops to ISE's 14a as described above. However, only member 38a is provided with grooves 42a and ridges 46a as before, the opposing member 40a having a substantially smooth surface 70. As further alternatives, the length of grooves 42a can extend from aperture 27a to aperture 27a', FIG. 5a, provided that the spacing between these two apertures is increased to prevent one drop from filling both apertures 28a and 28a' before the other is deposited. Also, grooves 42a can be eliminated, not shown, to form a smooth surface, and surface 70 can be retained as a smooth surface or can be grooved as in the embodiment of FIG. 2.

Figures 5B, 6, 7:
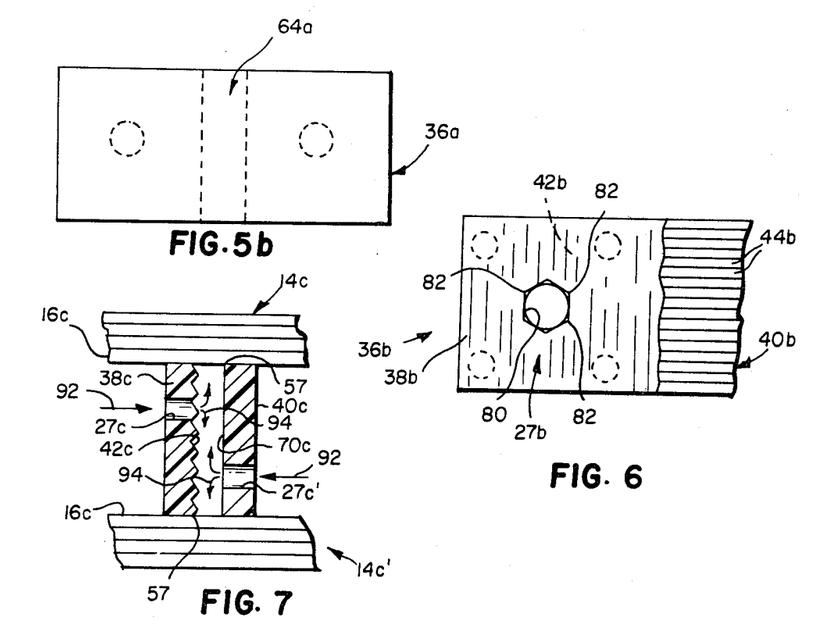
FIG. 5b is a plan view similar to FIG. 3 but illustrating the results of liquid transported by the device of FIG. 4.
FIG. 6 is a fragmentary plan view similar to that of FIG. 3 but illustrating a currently preferred embodiment.
FIG. 7 is an elevational view in section of still another embodiment of the invention.

It will be appreciated that, in the embodiments of FIGS. 4, 5a and 5b, the general smoothness of the surfaces of either or both members 38a and 40a leads to a generally unpredictable, undirected configuration for the advancing wave fronts 62a. The result is that the junction 64a which forms, FIG. 5b, is characterized by a relatively large width creating a wide diffusion zone that is relatively slow to reach equilibrium. It was thought that such a wide junction 64a would be likely to produce a significant bias in the form of a large and/or varying junction potential. In actuality, however, the electrical properties of ISE's 14a and 14'a are such that such a detrimental junction potential is not readily detectable.

However, it is contemplated that certain refinements may occur in the construction of the ISE's such that the shape and potential of junction 64a might become significant. In such a case, the embodiment of FIGS. 1-3 would be preferred as providing controlled predictable wave front peripheries that join to produce a minimum width junction 64.

FIG. 6 illustrates a currently preferred form of the liquid ingress apertures in exterior member 38b. Parts similar to those previously described bear the same reference numeral to which the distinguishing suffix "b" is appended. Thus, bridge 36b comprises upper or exterior member 38b and lower or interior member 40b. Each member has grooves 42b and 44b in its opposing surface, as previously described. However, as described in U.S. application Ser. No. 59,924, filed on July 23, 1979 entitled "Improved Structural Configuration and Method For Transport of a Liquid Drop Through an Ingress Aperture", now U.S. Pat. No. 4,254,083, issued on Mar. 3, 1981, the apertures through member 38b, of which only 27b is shown, are preferably formed by a cornered sidewall 80. That is, to drive a drop of liquid from the sidewall of the aperture into the center of the aperture, sidewall 80 is provided with a plurality of corners 82. Because of the surface tension of a deposited drop, such corners act as sites for increasing the centering vectors, thus driving the drops from the edge of the aperture into the aperture center. The fewer the number of corners, the less likely it is a drop will contact a corner and be affected. However, if too many corners are included, the aperture sidewall approaches a cylinder in shape, thus losing the benefit of the corner. Preferably, six corners 82 are utilized such that the aperture has the shape of a hexagon when viewed in plan.

The aperture 27b can have a variety of dimensions, but preferably for a drop volume of about 10 μl, it is about 0.25 cm between flats of the hexagon.

Aperture 28b of member 40b conveniently is cylindrical as in the previous embodiment, being aligned with aperture 27b as shown.

The device of the invention need not position the ion-flow bridge in a plane parallel to that of the planes of the ISE's nor need there be a total of four apertures through the bridge members. An alternate embodiment is illustrated in FIG. 7, wherein parts similar to those previously described bear the same reference numeral to which the distinguishing suffix "c" is appended. In this embodiment, the liquid communication between the transport zone and the ISE's does not comprise internal apertures through one of the members 38c or 40c. Instead, the transport zone itself provides the communication in that edges 57 of the zone terminate at ion-selective membrane 16c of each ISE 14c and 14'c. Thus, flow of each drop proceeds as shown by arrows 92 and 94, through apertures 27c and 27c', into the transport zone where capillary flow is controlled by the opposing surfaces of members 38c and 40c, and eventually to layers 16c of the ISE's. The opposing surfaces of members 38c and 40c can be smooth, as at 70c, or can have grooves such as grooves 42c.

Figure 8:
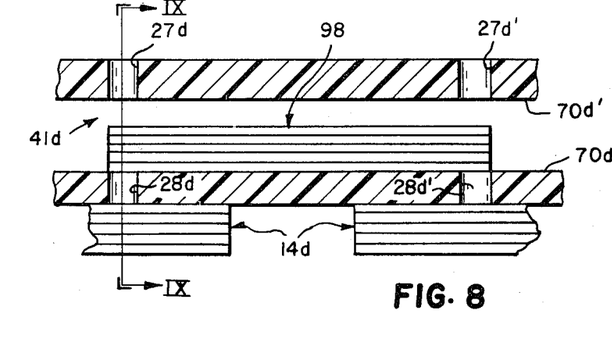
FIG. 8 is a sectional view similar to that of FIG. 4, but illustrating an alternate embodiment.
Figure 9:
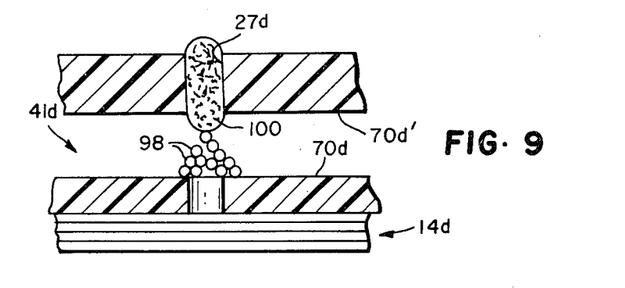
FIG. 9 is a fragmentary sectional view taken generally along the plane of line IX—IX of FIG. 8. Some of the fibers have been omitted for clarity.

The embodiment of FIGS. 8 and 9 illustrates that fibers can be used in the transport zone. Parts similar to those previously described bear the same reference numerals to which the distinguishing suffix "d" is attached. Thus, device 10d is the same as device 10a, FIG. 4, and alternatively can have any one of the aforedescribed grooved or smooth configurations for the two opposing surfaces. In addition, a fibrous material 98 is loosely disposed in zone 41d, the fibers being generally parallel and approximately straight, extending from at least aperture 27d to aperture 27d', FIG. 8. Preferably the fibers are coaxial and non-woven, and occupy no more than about 50% of the volume of zone 41d to permit transport of whole blood. The most preferred embodiment is one in which the fibers comprise only 5% of the volume of the zone. The alignment of the fibers from aperture 27d to aperture 27d' insures that the pressure loss due to interference to flow between the apertures is minimized. In this fashion, the fibers provide additional capillary transport surfaces to move the liquid from aperture 27d to aperture 27d', without being so closely packed that whole blood cannot be transported as the liquid. Such fibers are particularly useful when surfaces 70d and 70d' are low surface energy materials such as polystyrene. Filter tow fibers fabricated from cellulose acetate, for example, can be used.

Most preferably, the fibers extend out into the space under aperture 27d, so that they are in the flow path from the aperture 27d. As a result, the fibers are contacted by the meniscus 100, FIG. 9, as it comes out of the aperture. In this fashion the fibers help insure that the drop wets both surfaces 70d and 70d' and that flow through zone 41d is initiated.

The confinement of the fibers to an orientation that is generally perpendicular to the axis of apertures 27d and 27d' is sufficient to insure that no portions of the fibers extend through the lower apertures 28d and 28d' in a manner such as might permit liquid contact with the other ISE and cause a short.

Figure 10:
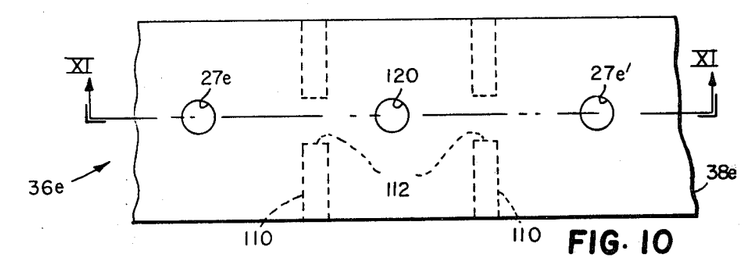
FIG. 10 is a fragmentary plan view similar to that of FIG. 3, but illustrating yet another embodiment.
Figure 11:
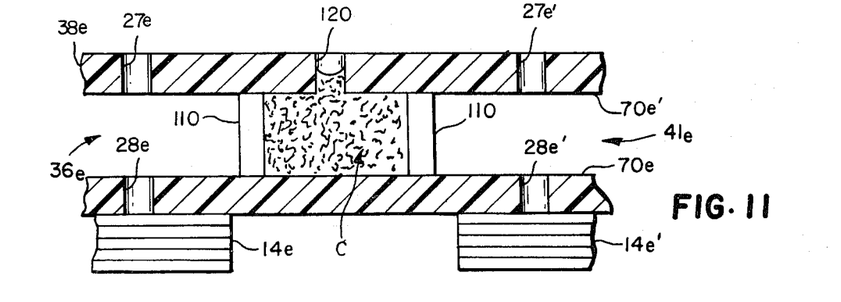
FIG. 11 is a sectional view taken generally along the plane of the line XI—XI of FIG. 10.

In the embodiment of FIGS. 10 and 11, a third passageway is provided intermediate the first two as a means for introducing a third liquid. Parts similar to those previously described bear the same reference numeral to which the distinguishing suffix "e" is applied. Thus, the device is provided as before with electrodes 14e and 14'e and bridge 36e apertures 27e, 27e' and 28e, 28e' acting as passageways into zone 41e and to the electrodes for the liquid from two drops. To restrict flow within the zone 41e, gating walls 110 extend from surface 70e to surface 70e'. Apertures 112 is the walls allow restricted flow between apertures 27e and 27e'.

In addition to the features of the previous embodiments, aperture 120 is included in member 38e of the bridge, approximately centered between apertures 27e and 27e'. This aperture allows the introduction of a third liquid C, FIG. 11, either before during or after the deposiof the two drops at apertures 27e and 27e'. Preferably a drop of the third liquid is applied prior to the deposition of the other two drops, and the volume of the third drop together with the restriction created by gating walls 110 act to confine the third liquid to the space between walls 110. Subsequently, the other two drops are applied and the entire zone 41e becomes filled.

Such an embodiment is particularly useful in applying an equitransferent salt solution of the type described in U.S. Pat. No. 4,053,381, issued on Oct. 11, 1977. The salt solution acts to suppress junction potentials when the two ionic solutions meet within the zone 41e.

As an alternate to applying the third drop to aperture 120 immediately prior to the application of the other two drops, the third solution can be added and allowed to dry, coating surfaces 70e and 70e' between the gating walls 110. The salts of the coating then re-dissolve as the two test drops spread through the zone. Or as a further alternative, a gelatinous solution containing the salts can be introduced through aperture 120 and allowed to "set".

Figures 12, 13:
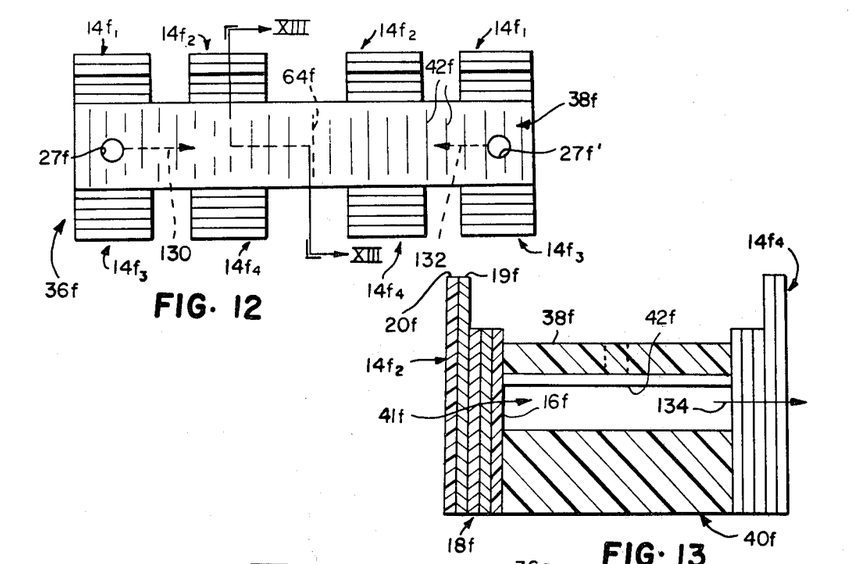
FIG. 12 is a plan view of still another embodiment of the invention.
FIG. 13 is a sectional view taken generally along the plane of line XIII—XIII of FIG. 12.

In the embodiment of FIGS. 12 and 13, more than one ionic analyte is tested from a single drop by incorporating at least one other pair of electrodes into the device adjacent to the first pair. Parts similar to those previously described bear the same reference numeral to which the distinguishing suffix "f" is applied. Thus, the flow control means is bridge 36f comprising upper or exterior member 38f and lower or interior member 40f, FIG. 13, which may or may not be mounted on a larger support (not shown). In the absence of such a support, member 40f has a thickness which renders it self-supporting. Each such member 38f and 40f may or may not have exposed grooves in the opposing surfaces; e.g., grooves 42f, FIG. 13, as described previously, and apertures 27f and 27f' are located in member 38f as liquid drop inlet apertures, as described for previous embodiments. However, no corresponding pair of apertures exists in member 40f. Instead, the pairs of ISE's 14$f_1$, 14$f_2$, 14$f_3$ and 14$f_4$ are disposed along the exposed sides of a capillary transport zone 41f that is formed in the following manner, similar to the embodiment shown in FIG. 7.

Zone 41ƒ is confined in the vertical direction between members 38ƒ and 40ƒ, and horizontally between ISE pairs 14ƒ₁ etc. To space apart members 38ƒ and 40ƒ, the pairs of ISE's are adhered to the side edges of members 38ƒ and 40ƒ by a suitable adhesive, and are disposed so that they also are spaced apart and electrically isolated. The ion-selective membranes or substitute layer 16ƒ of the ISE's, FIG. 13, are all directed inwardly towards the zone to permit contact of the liquid as the two drops move through zone 41ƒ from the inlet apertures along paths 130 and 132 (FIG. 12). The space between the ISE's comprises vent apertures that permit air to exit from the zone as indicated by arrow 134, FIG. 13, as the two drops fill the zone.

To facilitate contact between the electrodes and a potentiometer, conductive layer 19ƒ and support layer 20ƒ can be formed to extend upwards beyond adjacent layer 18ƒ, FIG. 13.

Because one of each pair of electrodes must contact the drop deposited at aperture 27ƒ, and the other of each pair must contact the drop deposited at aperture 27ƒ', the pairs are split so that one of electrode pairs 14ƒ₁, 14ƒ₂, 14ƒ₃ and 14ƒ₄ is adjacent to aperture 27ƒ and path 130 and the other of each pair is adjacent to aperture 27ƒ' and path 132. The sequence of electrodes around each aperture is not critical. Of course, it is preferred that the junction between the two drops form generally in the middle of bridge 36ƒ, between the members of the paired electrodes, as at 64ƒ, FIG. 12. For this reason the grooves, if any, of members 38ƒ and 40ƒ should be designed to insure flow rates that will locate junction 64ƒ as described. Alternatively, a plurality of gating walls, not shown, such as are described in the embodiment of FIG. 10, can be used.

Each of the electrode pairs is specific to the analysis of a different one of the analytes. For the differential mode of measurement, each electrode of any pair is identical to the other of the pair. Thus, the electrodes for electrode pair 14ƒ₁ can be constructed and adapted to detect $K^{\oplus}$, the two electrodes for pair 14ƒ₂ to detect $Na^{\oplus}$, the two electrodes for pair 14ƒ₃ to detect $Cl^{\ominus}$, and the two electrodes for pair 14ƒ₄ to detect $HCO_3^{\ominus}$. The chemistires of the layers of the electrodes are not part of this invention, and comprise generally that described above for ion $Z^{\oplus}$ with the appropriate selection of an ionophore for layer 16ƒ. For example, in the case of the $K^{\oplus}$ electrodes, layer 16ƒ contains an ionophore such as valinomycin or one of the others listed in *Research Disclosure*, Vol. 161, Publication No. 16113, September 1977, 2nd col. of p. 32, published by Industrial Opportunities Limited, Homewell, Havant Hampshire PO91EF, United Kingdom, the contents of which are expressly incorporated herein by reference. For the $Na^{\oplus}$ electrodes, the ionophore is preferably methyl monensin, and for $HCO_3^{\ominus}$ the ionophore is preferably 4-octyl trifluoroacetophenone and the solvent is trioctyl propylammonium chloride. For the $Cl^{\ominus}$ electrodes, layers 16 and 17 are replaced by an interferant-barrier overcoat layer. Such overcoat layer can be, e.g., cellulose acetate containing a polyol.

In use, the drop of sample to be tested is deposited in one of apertures 27ƒ and 27ƒ' and the reference drop in the other. The drops spread by capillary action along the paths of arrows 130 and 132, contacting the electrodes and eventually each other at junction 64ƒ. Readings can be made by contacting layer 19ƒ of each electrode in a given pair with the probes of an electrometer.

The spacing between members 38ƒ and 40ƒ should be as described previously. The width of zone 41ƒ, e.g., the distance between ISE's 14ƒ₁ and 14ƒ₃, can be widely varied, preferably between about 5 and 15 mm. The total length of zone 41ƒ is a matter of choice.

Yet another embodiment of the invention permits the so-called "absolute" measurement of the analyte activity. The embodiment is that of FIGS. 12 and 13, except that one of the eight electrodes 14ƒ₁ through 14ƒ₄ is a common, general reference electrode for all the other electrodes, and each of the other electrodes is an ISE of the type described in previous embodiments, designed to measure with that general reference electrode a particular analyte different from the analytes tested by the others. A preferred example of such a general reference electrode uses a redox couple element of the type described in connection with FIG. 14 of aforesaid U.S. Pat. No. 4,053,381, the details of which are expressly incorporated herein by reference. Only a single aperture 27ƒ or 27ƒ' is needed, and is preferably centrally located. A single drop of test liquid is applied and the transport zone distributes the liquid of that drop to all the electrodes, including the general reference electrode. For a reading, the two probes of the electrometer contact, respectively, the conductive metal layer of the general reference electrode and of the one of the other electrodes appropriate to the analyte under study.

Figure 14:
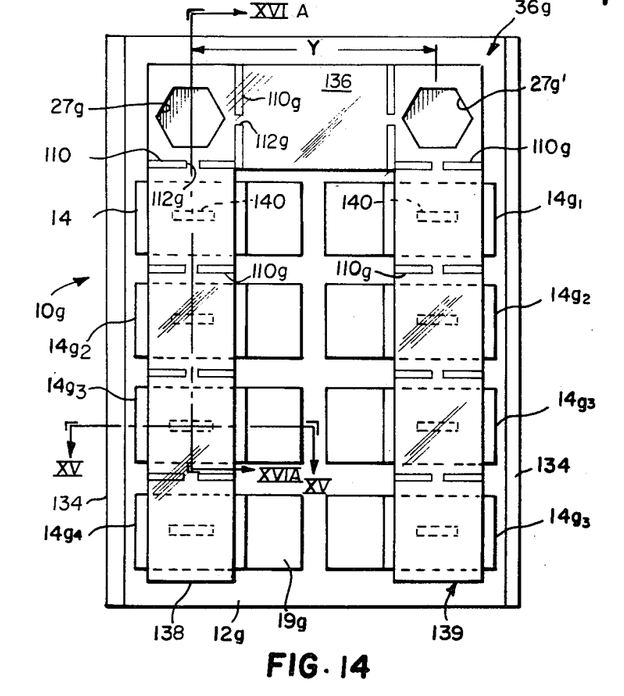
FIG. 14 is a plan view similar to that of FIG. 12 but illustrating another embodiment.
Figure 15:
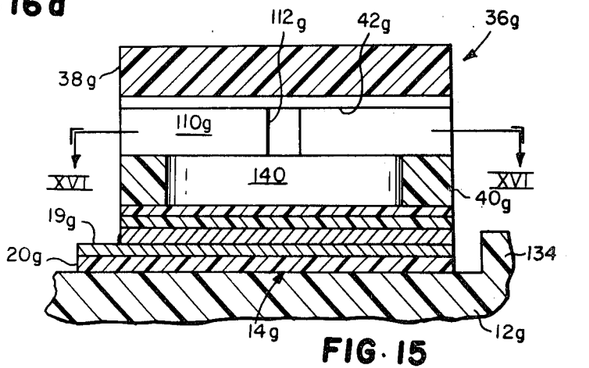
FIG. 15 is a sectional view taken along line XV—XV of FIG. 14.

In FIGS. 14–16, a preferred embodiment of the multianalyte test device of FIGS. 12 and 13 is illustrated. Parts similar to those previously described bear the same reference numeral to which the distinguishing suffix "g" is applied. The device 10g comprises a frame 12g having opposite side ribs 134, a bridge member 36g and a plurality of ISE's 14g exactly as described for the other multi-analyte embodiments, except that each of the ISE's is located under lower member 40g of the bridge, FIG. 15, rather than at the sides of the transport zone 41g. Furthermore, to minimize the space that is occupied, bridge 36g has been shaped as a horseshoe, with a central portion 136 and two dependent legs 138 and 139, FIG. 14. The pairs of ISE's are conveniently arranged opposite each other on legs 138 and 139, e.g., ISE's 14g₁ aligned opposite each other, 14g₂ opposite each other, and so forth. The spacing between adjacent ISE's can be uniform as shown, or varied. Upper member 38g of the bridge is preferably grooved as at 42g, FIG. 15. Gating walls 110g are disposed in zone 41g between each ISE, FIG. 16a, and between apertures 27g and 27g' and those apertures and the first ISE pair 14g₁, FIG. 14. Each gating wall has an aperture 112g, and serves to join members 38g and 40g in a spaced apart relationship as in previous embodiments. The electrometer probes can contact the ISE's at the protruding layer 19g, FIG. 15.

It is preferred that the flow patterns controlled by gating walls 110g and the distance "Y" between the centers of apertures 27g and 27g', FIG. 14, be such that the two drops meet in portion 136 between the apertures prior to the liquid of either drop contacting the ISE's 14g₁.

Figure 16:
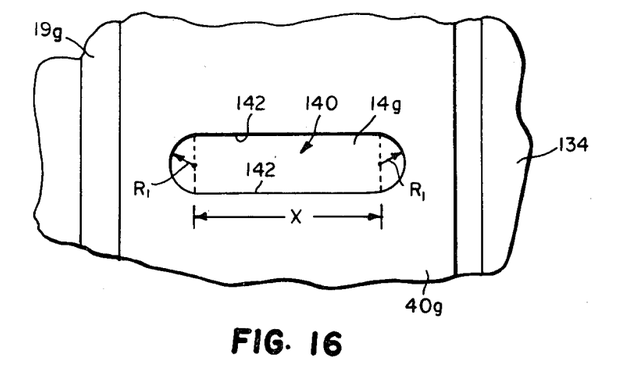
FIG. 16 is a fragmentary sectional view taken generally along the line XVI—XVI of FIG. 15.

Because ISE's 14g are located under member 40g, a specially designed flow aperture 140 is included in member 40g, superimposed directly above each ISE, FIGS. 15 and 16. It is this aperture which carries advancing liquid such as blood or blood serum away from zone 41g down into contact with the ISE's. To insure the meniscus of the liquid will completely wet and fill the aperture 140, and therefore the exposed area of the ISE, such aperture preferably has the shape as shown in FIG. 16, namely two parallel sides 142 that close onto one another with two curved surfaces each having a radius of curvature "$R_1$" generated from centers of curvature that are spaced apart a distance "x". The most preferred dimensions for aperture 140 are x=1.5 mm and $R_1$=0.228 mm, although $R_1$ can be as large as 0.5 x. Alternatively, aperture 140 can be a rectangle as shown in phantom, FIG. 16. For best results, the depth of aperture 140 through which the liquid travels to contact the ISE 14g is preferably 125 microns or less.

Figure 16A:
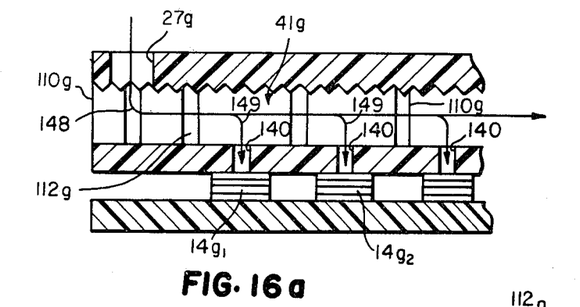
FIG. 16a is a fragmentary sectional view taken generally along the line XVIA—XVIA of FIG. 14.

FIG. 16a illustrates the flow pattern from, e.g., aperture 27g. The capillary spacing of zone 41g, enlarged in the figure, causes the drop to follow arrow 148 through each of the gating apertures 112g, and a portion of the liquid also follows arrows 149 through apertures 140 into contact with the ISE's $14g_1$, $14g_2$, etc.

Figure 17:
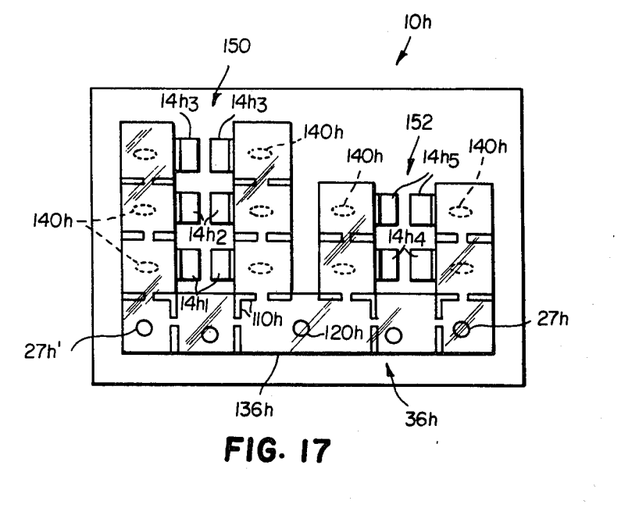
FIG. 17 is a plan view similar to that of FIG. 14 but illustrating still another embodiment.

The embodiment of FIG. 17 demonstrates how the device of FIGS. 14–16 can be modified to permit two different unknown liquids to be tested on the same test element device 10h, using a common reference liquid. Parts similar to those previously described bear the same reference numeral to which the distinguishing suffix "h" is applied.

The increased capability of device 10h is achieved by a doubling of bridge 36h to include two banks 150 and 152 of paired electrodes 14h, rather than just one, each bank being connected to the other by bridge portion 136h having a third aperture 120h as in the embodiment of FIG. 11. Bank 150 has paired electrodes $14h_1$, $14h_2$, and $14h_3$, while bank 152 has paired electrodes $14h_4$ and $14h_5$. Apertures 27h and 27h', apertures 140h, and gating walls 110h are constructed in the manner described for previous embodiments.

In operation, a drop of blood serum from a first patient is deposited in aperture 27h' while a drop of reference liquid is deposited in aperture 120h and a drop of whole blood from patient A, or of blood serum from patient B, is deposited in aperture 27h. The reference liquid serves to keep the two different blood samples apart, and yet the one drop of reference liquid supplies all the reference potential needed for both tests. By the sample addition of another bank of ISE's extending from portion 136h in a direction opposite to the direction of banks 150 and 152, yet a third patient sample could be simultaneously tested on device 10h.

The embodiments of FIGS. 18–22 feature a particularly facile form of the invention for rapid and inexpensive manufacture. Parts similar to those previously described bear the same reference numeral to which the distinguishing suffix "k" is attached. Thus, device 10k, FIG. 18, comprises two ISE's 14k constructed as described previously and adhered or otherwise attached to the bottom surface 200 of a frame member 12k, the electrodes being spaced apart to provide electrical isolation. The frame member has a bridge 36k that is an integral portion thereof, comprising an internal capillary transport zone 41k defined by two opposed, generally smooth surfaces 70k and 70k' spaced apart the distance s, FIG. 19, for providing ionic flow between drops A and B. As in the previous embodiments, zone 41k extends from zone edges 56k to 56k, and from zone edges 57k to 57k, the latter coinciding with the side surfaces 210 of device 10k.

It will be recognized that, as with previous embodiments, either surface 70k or 70k' can alternatively be provided with preferably linear and parallel grooves, not shown. If both surfaces are grooved, the grooves of one surface can be either aligned with or at an angle to those of the other.

Liquid inlet apertures 27k and 27k' are formed in bridge 36k as before, extending from top surface 214 of the frame member to surface 70k' of the transport zone. Apertures 28k and 28k', FIG. 19, constitute the liquid passageways extending from zone 41k to ISE's 14k. Preferably, each of the paired apertures 27k and 28k, and 27k' and 28k', is formed as a single aperture extending from top surface 214 to bottom surface 200, interrupted however by zone 41k.

Figure 19:
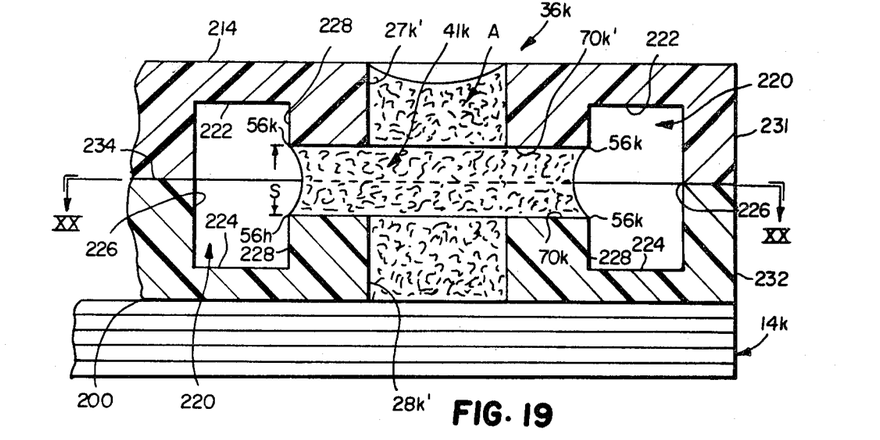
FIG. 19 is a fragmentary sectional view taken generally along the vertical plane of the line XIX—XIX of FIG. 18.

To vent trapped air away from zone 41k as the zone fills with aqueous solution, a separate vent channel 220 is fluidly connected to zone 41k at edges 56k, FIG. 19, each such channel comprising top and bottom surfaces 222 and 224, and side wall surfaces 226 and 228. Surfaces 222 and 224 are spaced apart a distance greater than distance s, and wall surfaces 228 join surface 70k at intersection edges 56k, at an angle that is sufficient to inhibit movement of the liquid out of zone 41k into channel 220. Preferably, such angle is about 90°.

Figure 18:
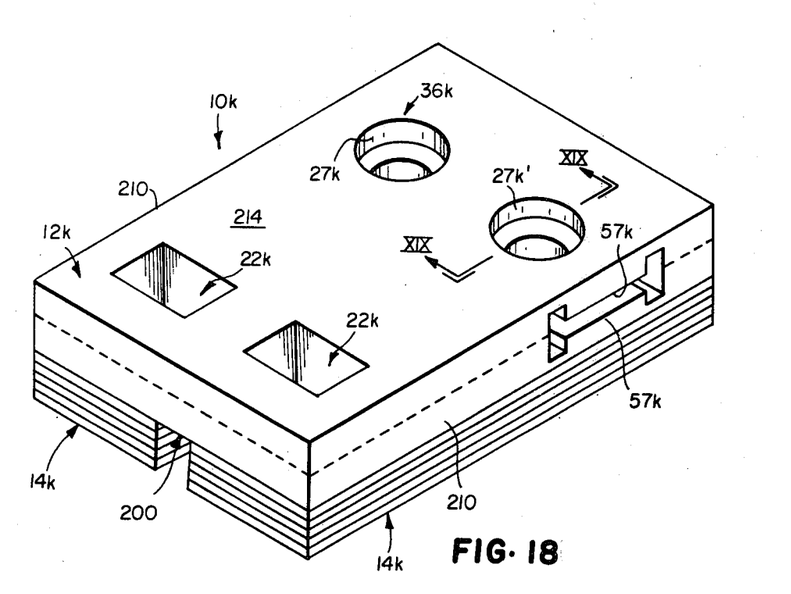
FIG. 18 is an isometric view of yet another embodiment of the invention.

To allow operative contact by an electrometer with ISE's 14k, apertures 22k, FIG. 18, extend completely through frame member 12k from top surface 214 to bottom surface 200 and the two electrodes 14k, respectively.

Figures 20A, 20B, 20C:
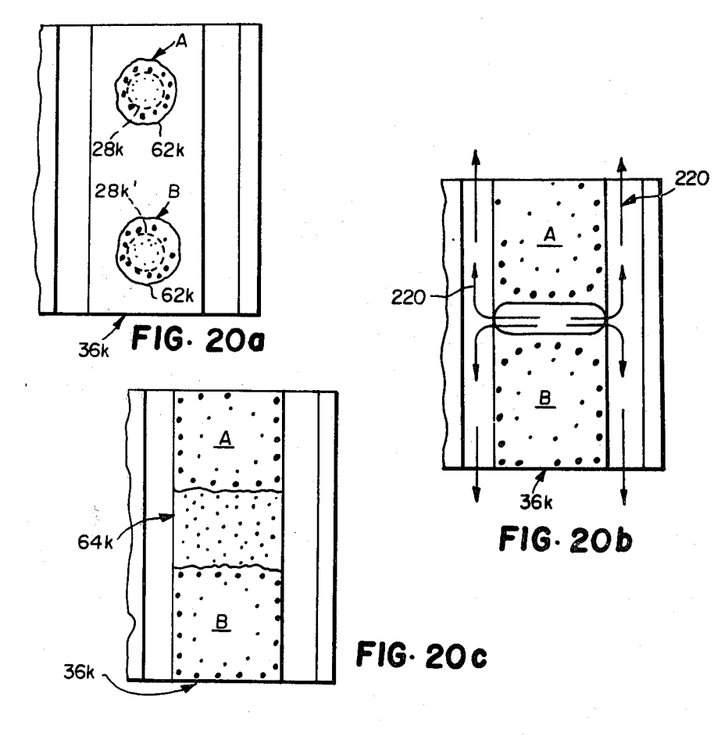
FIGS. 20a-20c are fragmentary plan views taken as sections along the horizontal plane of line XX—XX of FIG. 19, illustrating the pattern of liquid transport that occurs in the device of FIGS. 18 and 19.
Figures 21, 22A, 22B, 22C:
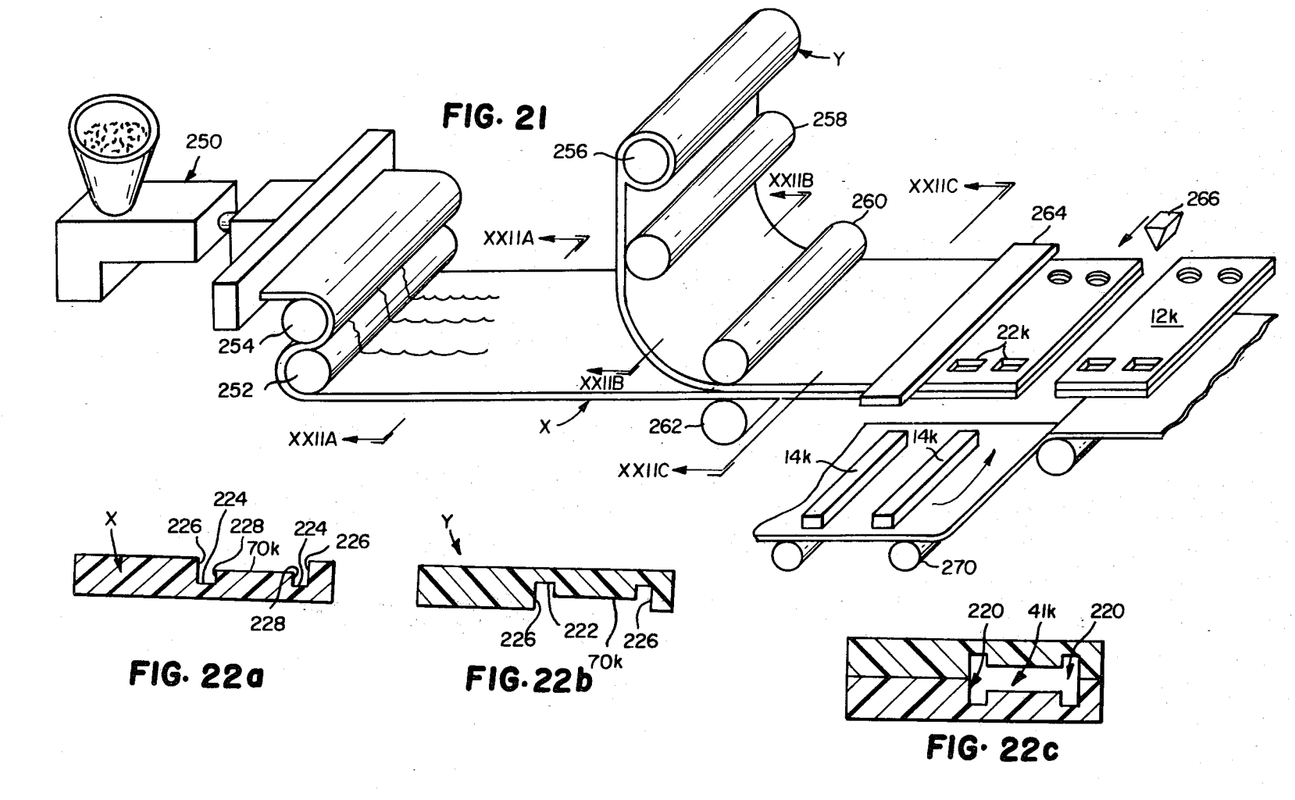
FIG. 21 is a partially schematic, isometric view of apparatus and a process that can be used to continuously manufacture the device of FIGS. 18-19.
FIGS. 22A-22C are sectional views taken along the planes of the lines XXIIA—XXIIA, XXIIB—XXIIB, and XXIIC—XXIIC, respectively, of FIG. 21.

The stages of liquid transport using bridge 36k having ungrooved surfaces 70k are indicated in FIGS. 20a through 20c. When the liquids A and B, such as blood serum or whole blood, are first deposited in aperture 27k and 27k', they spread somewhat randomly and curvilinearly as shown by irregular wave fronts 62k, FIG. 20a. This is the result of random minor irregularities in the generally smooth surfaces 70k and 70k'. As the liquid is further transported by capillary attraction, edges 56k are reached, FIG. 20b, where the surface tension of the liquid interacts with the barriers created by the edges to halt the movement of the liquid wave fronts. Air that is in the process of being trapped between the two liquid bodies A and B flows out through vent channels 220. Eventually the two solutions A and B meet to form a junction 64k, FIG. 20c, which because of the irregularities of the wave fronts of the transported liquids A and B has a significant width representing considerable intermixing. Alternatively such intermixing and junction width can be reduced if desired by incorporating grooves into one or both of surfaces 70k and 70k'.

The formation of the junction 64k, together with contact of solutions A and B with ISE's 14k, FIG. 19, completes the electrical circuit via the flow of ions, and an electrometer reading can be made.

Alternatively, a fibrous material, not shown, of the type described in the embodiment of FIG. 8, can be loosely disposed within zone 41k.

As yet other alternatives, not shown, one of the vent channels 220 can be omitted, the other channel being adequate to allow removal of trapped air. Or, the frame need not be integral with the bridge as in FIG. 18, and yet the bridge can incorporate vent channels as shown in FIG. 18. In such an arrangement the bridge 36 of the device of FIG. 1 would be replaced by just the bridge 36k shown in FIG. 19.

Still another alternative, not shown, is to ultrasonically seal edges 57k together at each end of bridge 36k, thereby closing zone 41k to the atmosphere except through the apertures extending outwardly from surface 70k'. If this is done, a plurality of small air vents should be included extending between surface 70k' and surface 214, disposed between aperture 27k and the side surface 210 adjacent thereto, between aperture 27k' and the side surface 210 adjacent thereto, and between the two apertures 27k and 27k'. Such air vents, where used, can be considerably smaller in diameter than apertures 27k and 27k', as they serve only to release trapped air. For maximum venting effect, the vents can be disposed in the shape of an "X", not shown, in surface 214.

As will be seen from FIG. 18, FIG. 19 and FIGS. 22A–C, frame member 12k can be formed as two halves 231, 232 that are symmetric about a plane 234, FIG. 19. Such a construction permits the use of a process of manufacture such as is shown in FIGS. 21 and 22A–C. That is, to provide a first sheet X of formable material, an extruder 250 ejects sheet X which is passed through two forming rolls 252 and 254. These rolls in turn groove sheet X to the cross-sectional shape shown in FIG. 22A, that is, with depressed surfaces 70k (or 70k'), 222 (or 224), 226 and 228. From rolls 252 and 254 sheet X is either removed to become a rolled from Y on axle 256, or it is passed continuously under a roller 258 that feeds into position an identical but inverted sheet Y already formed with the cross-sectional shape of FIG. 22B. The two sheets X and Y are then secured to each other except for zone 41k and channels 220, FIG. 22C, by pressure rolls 260 and 262, with or without the use of a conventional adhesive, depending on the material of sheets X and Y. A flying punch 264 forms apertures 22k as well as apertures 27k, 28k, and 27k', 28k', preferably a pair at a time, FIG. 21. To sever the secured sheets to form individual units, each comprising a completed frame member 12k, a flying cutter 266 is positioned down-stream of the punch. Meanwhile a conveyor belt 270 carries a pair of preferably identical ISE's 14k into a contacting position below frame member 12k, where the frame member and ISE's are joined such as by an adhesive, not shown, preapplied to the ISE's.

Alternatively, the apertures can be formed after individual units are severed, and the ISE's can be attached before the severing of the units.

As will be readily apparent, such a process has the advantage of being continuous, although it can also be operated as a batch process.

The invention has been described in detail with particular reference to certain preferred embodiments thereof, but it will be understood that variations and modifications can be effected within the spirit and scope of the invention.

What is claimed is:

1. A method for making a device for the determination of activity of an ionic analyte of a liquid, said device including a pair of solid electrodes each constructed to generate therein an electrical potential that is proportional to the analyte activity present in a contacting quantity of said liquid, and flow control means for directing flow of respective quantities of two such liquids each to a different one of said electrodes and to a junction between said liquids, said control means including a member bridging and contacting said two electrodes; the method comprising the steps of
   (a) providing a first sheet of formable insulative material having a width and length;
   (b) forming in said sheet a plurality of adjacent channels extending generally the length of said sheet, a surface of one of said channels being configured to transport liquid;
   (c) superimposing above said formed sheet a second insulative sheet a surface portion of which is channeled to transport liquid and is opposite to and spaced away from said one surface a distance effective to induce capillary flow of the liquid between said portion and said one channel surface;
   (d) securing said second sheet to said first sheet to define a capillary liquid transport zone extending in the direction of the length of said first sheet; and, in any order,
   (e) forming apertures extending all the way through said secured first and second sheets;
   (f) severing individual units from said secured sheets; and
   (g) completing the manufacture of a plurality of said devices by attaching a pair of said electrodes to an exterior surface of said first sheet of each of said individual units, each of said electrodes being aligned with one of said apertures.

2. A method as defined in claim 1, wherein said second sheet is the mirror image of said first sheet.

3. A method as defined in claim 1 or 2, wherein said sheets are formed by extrusion.

4. A method as defined in claim 1 or 2, wherein at least each of said steps (a) and (b) is performed as a continuous process.

5. A method as defined in claim 1, wherein said channels of said sheet are at least 95% void by volume.

* * * * *